US00PP24435P2

(12) United States Plant Patent
Davidson et al.

(10) Patent No.: US PP24,435 P2
(45) Date of Patent: May 13, 2014

(54) ROSE PLANT NAMED 'CA 29'

(50) Latin Name: *Rosa hybrida*
Varietal Denomination: CA 29

(75) Inventors: Campbell G. Davidson, West Hawk Lake (CA); Larry J. Dyck, Morden (CA)

(73) Assignee: Her Majesty the Queen in right of Canada, as represented by the Minister of Agriculture and Agri-Food, Lancombe, Alberta (CA)

( * ) Notice: Subject to any disclaimer, the term of this patent is extended or adjusted under 35 U.S.C. 154(b) by 90 days.

(21) Appl. No.: 13/573,187

(22) Filed: Aug. 29, 2012

(51) Int. Cl.
*A01H 5/00* (2006.01)

(52) U.S. Cl.
USPC ..... Plt./102; Plt./101

(58) Field of Classification Search
USPC ..... Plt./102, 101
See application file for complete search history.

*Primary Examiner* — Susan McCormick Ewoldt
(74) *Attorney, Agent, or Firm* — Penny O. Aguirre

(57) ABSTRACT

A new cultivar of shrub rose, 'CA 29', characterized by its semi-double flowers that open medium yellow in color with pink margins, maturing to medium pink with dark pink margins and fading to a cream color with dark pink margins; creating a multicolored effect, its flower buds that are medium yellow in color with dark pink margins, its continuous blooming habit, its glossy foliage with good resistance to powdery mildew, rust and black spot, and its cold hardiness at least to U.S.D.A. Zone 3a.

2 Drawing Sheets

Botanical classification: *Rosa hybrida.*
Variety denomination: 'CA 29'.

BACKGROUND OF THE INVENTION

The present invention relates to a new and distinct cultivar of *Rosa hybrida*. The new cultivar will be referred to hereafter by its cultivar name, 'CA 29'. 'CA 29' is a new cultivar of shrub rose grown for use as a landscape shrub.

The new cultivar of shrub rose is a selection from a controlled breeding program conducted by the Inventors in Morden, Manitoba, Canada with an objective to create new rose cultivars with greater hardiness, greater disease resistance, ever blooming habits, and unique flower colors.

The new variety of shrub rose, 'CA 29', was selected by the Inventors from amongst 444 seedlings derived from a cross made in March 2003 between the female parent, 'BAIhero' (U.S. Plant Pat. No. 15,400) and the male parent, 'Frontenac' (U.S. Plant Pat. No. 9,210). 'CA 29' was selected as a single unique plant in September of 2005.

The new cultivar was first asexually propagated by one of the Inventors by softwood cuttings in Morden, Manitoba, Canada in September 2005. Asexual propagation determined that the characteristics of this cultivar are stable and are reproduced true to type in successive generations.

SUMMARY OF THE INVENTION

The following traits have been repeatedly observed and represent the characteristics of the new shrub rose as observed in Morden, Manitoba, Canada. These attributes in combination distinguish 'CA 29' as a unique cultivar of shrub rose.

1. 'CA 29' exhibits semi-double flowers that open medium yellow in color with pink margins, maturing to medium pink with dark pink margins and fading to a cream color with dark pink margins.

2. 'CA 29' exhibits flowers with three distinct colors on the same plant with flowers in different stages of maturity creating a multicolor effect to the plant in bloom.
3. 'CA 29' exhibits flower buds that are medium yellow in color with dark pink margins.
4. 'CA 29' is floriferous with a continuous blooming habit; blooming from the middle of June to early October in Morden, Manitoba, Canada.
5. 'CA 29' exhibits glossy foliage.
6. 'CA 29' exhibits cold hardiness at least to U.S.D.A. Zone 3a.
7. 'CA 29' has shown very good resistance to powdery mildew, rust, and black spot.

The new cultivar of shrub rose can be readily distinguished from its parents. The female parent, 'BAIhero', differs from 'CA 29' in having red flowers that are more double, less cold hardiness and vigor, and in being less disease resistant. The male parent, 'Frontenac', differs from 'CA 29' in having medium pink flowers (lacks yellow and cream coloration) and a more compact plant habit. 'CA 29' can also be most closely compared to the cultivars 'BAIset' (U.S. Plant Pat. No. 16,770) and 'Morden Sunrise' (U.S. Plant Pat. No. 13,969). 'BAIset' is similar to 'CA 29' in plant habit and bloom period and in having flowers that open yellow with pink margins, but differs from 'CA 29' in having flowers that fade to pink with yellow tinges, in having much less cold hardiness, and in being less disease resistant. 'Morden Sunrise' is similar to 'CA 29' in having flowers and flower buds that are yellow with pink margins, but differs from 'CA 29' in having flowers that fade to light yellow, in being less floriferous, and in having less cold hardiness, disease resistance, and vigor.

BRIEF DESCRIPTION OF THE DRAWING

The accompanying colored photographs illustrate the overall appearance and distinct characteristics of the new shrub rose, 'CA 29'. The photographs were taken of three year-old plants of 'CA 29' and 'BAIset' as grown outdoors near Portage la Prairie, Manitoba, Canada.

The photograph in FIG. 1 provides a view of newly open flowers of 'CA 29'.

Figure 1:
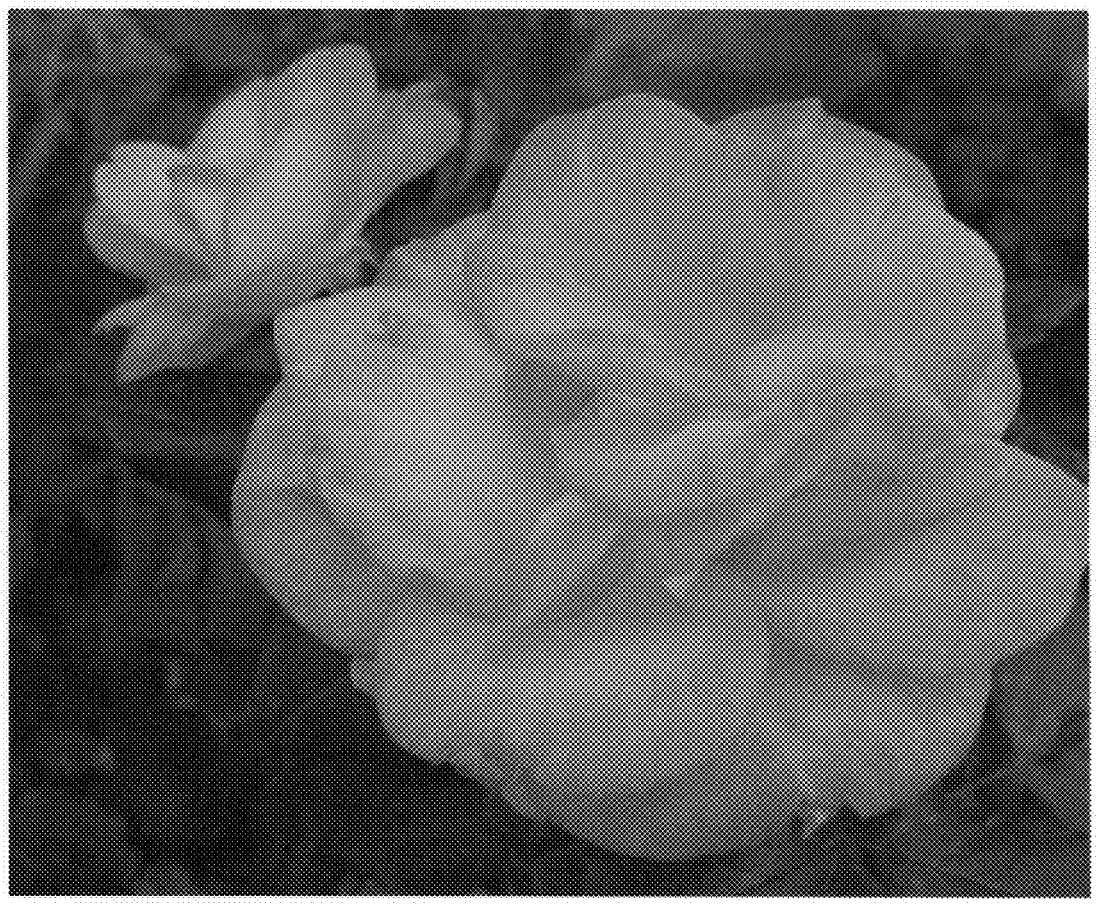
Figure 2:
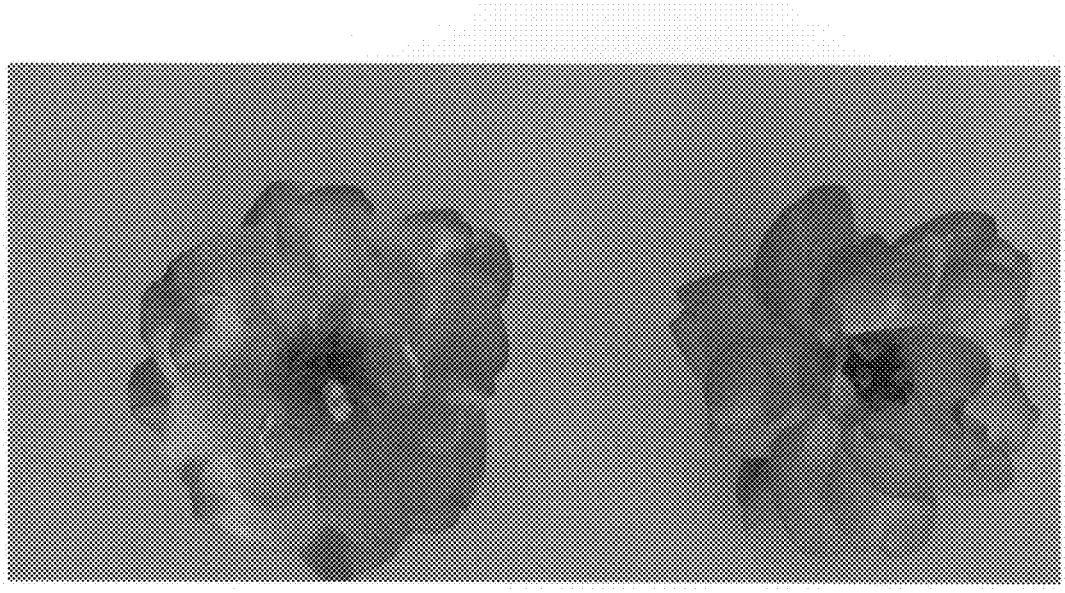

The photograph in FIG. 2 provides a view of a mature flower of 'CA 29' (left) in comparison to a mature flower of 'BAIset'.

The colors in the photographs are as close as possible with digital photography techniques available, the color values cited in the detailed botanical description accurately describe the colors of the new shrub rose.

DETAILED BOTANICAL DESCRIPTION

The following is a detailed description of two year-old plants the new cultivar as grown outdoors in 2-gallon containers in St Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Continuous bloom from the middle of June to early October in Morden, Manitoba, Canada.

*Plant type*.—Deciduous shrub.

*Plant habit*.—Moderately spreading.

*Height and spread*.—An average of 43 cm height and 40 cm width in a 2-gallon container, matures in the landscape to about 76 cm in height and 114 cm in spread.

*Cold hardiness*.—At least to U.S.D.A. Zone 3a.

*Diseases and pests*.—Has shown very good resistance to powdery mildew, rust, and black spot.

*Propagation*.—Softwood stem cuttings.

*Growth rate*.—Moderate.

Branch description:

*Stem color*.—Young; 144A maturing; a blend of 146B and 146C, mature wood; ridges of 200A and 199D.

*Stem surface*.—Young; glabrous, mature; slightly glaucous, adult wood; finely barked.

*Branching*.—1 to 3 lateral branches per stem, 8 stems per 2-gallon container.

*Stem size*.—Average of 6 mm in width, up to 30 cm in length.

*Thorns*.—Shape triangular, aspect slightly downward, base oval, average of 4 in number per stem 15 cm in length, average of 4 mm in length with a base 4 mm in length and 3 mm in width, 199D in color.

Foliage description:

*Leaves*.—Division is odd-pinnate, arrangement is alternate, average of 9 cm in length and 6 cm in width, internode length is an average of 3 cm.

*Leaflets*.—5 to 7, average of 3 cm in length and 2 cm in width, broadly elliptic to ovate in shape, rounded base, acute to acuminate apex, serrated margins, color emerging leaves upper surface; 144A, color emerging leaves lower surface; a color between 144A and 138B, color young and mature leaves upper surface; a blend of 137A and 144A, color young and mature leaves lower surface; 138B, pinnately veined (not conspicuous) mid rib 144A on upper surface and 138C on lower surface, surface glabrous and glossy on upper surface and glabrous and dull on lower surface.

*Rachis*.—Average of 6 cm in length and 1 mm in diameter, color between 144B and 138B upper surface and lower surface with center of upper surface suffused with 183B, surface is glabrous on upper and lower surface with a few sparse long hairs on upper surface.

*Stipules*.—Aspect outward with auricle facing upward, adnate to petiole, average of 1 cm in length and 4 mm in width, color upper and lower surface; 144B and suffused with 183B, surface is glabrous on upper surface and lower surface.

*Petioles and petiolules*.—Petioles; an average of 1.8 cm in length and 1.5 mm in diameter, petiolules; an average of 2 mm in length and 1 mm in diameter, petioles and petiolules; color on mature leaves upper surface; 144A suffused with 183B, color on mature leaves lower surface; between 144B and 138B, surface glabrous on upper and lower surfaces.

Inflorescence description:

*Inflorescence type*.—1 to 2 flowers per lateral branch, semi-double flowers.

*Flower number*.—Average of 5 per main stem.

*Flower fragrance*.—Weak rose scent.

*Flower longevity*.—About 8 days, depending on temperature and sunlight exposure.

*Flower type*.—Semi-double, rosette in form.

*Flower size*.—Average of 8.3 cm in diameter and 3.5 cm in depth.

*Peduncles*.—Round in shape, average of 3 cm in length and 1.8 mm in diameter, glabrous and satiny surface, 144B in color.

*Bracts*.—2, at base of peduncle, narrowly deltoid in shape with long apiculate apex, cuneate base, margin glandular, an average of 1.2 cm in length and 6 mm in width, a blend of 144A and 137C in color on upper and lower surface, glabrous on both surfaces with a few long fine hairs on margin.

*Flower buds*.—Ovate in shape, an average of 3 cm in length and 1.7 cm in width prior to opening, color 11A and suffused with margin of petals 45D, sepal portion a blend of 144A and 137B.

*Sepals*.—5, triangular in shape, margin entire, color of upper surface; 138B, color of lower surface; a blend of 144A and 137B, average of 2.7 cm in length and 7 mm in width, acuminate apex, truncate base, reflexed to stem on mature flowers, upper pubescent on upper surface, glabrous and satiny on lower surface.

*Petals*.—An average of 14 per flower, drop readily and cleanly, obcordate to rounded in shape, upper and lower surface glabrous, margin entire and slightly undulating, base broadly cuneate, apex is rounded and occasionally with a notch, average of 3 cm in length and width, color: opening flowers upper and lower surface; 5D with base 5B and suffused irregularly with 50B and 50C (stronger on margins and lower surface of lower petals), fully open flowers upper and lower surface; a blend of 5D and 4D with base 5B and suffused with 50B and 50C (most prominently near petal margins), fading flowers upper and lower surface; a blend of 4D and N155D with very base 5B and suffused slightly with 50C (most prominently near petal margins).

*Receptacle*.—Average of 8 mm in diameter and 1.5 mm. in depth when flower is fully open, flat disk shaped, waxy surface, 2A in color.

*Pistils*.—About 28 per flower, stigma is an average of 0.6 mm in diameter and 153D in color, style is an average of 2 mm in length and 153D in color, no petaloid pistils, ovary is cone-shaped, 9 mm in length and 6 mm in width and 144A in color, glossy surface.

*Stamens*.—About 70, filaments are about 7 mm in length and 12A in color, anthers are an average of 2.5 mm in length, an average of 1.5 mm in width and 17D in color, pollen is abundant in quantity and 17A in color.

*Hips*.—Pitcher-shaped in longitudinal section, not distinguishing or showy.

It is claimed:

1. A new and distinct cultivar of rose plant named 'CA 29' as herein illustrated and described.

* * * * *